(12) United States Patent
Wenchell

(10) Patent No.: US 8,328,844 B2
(45) Date of Patent: Dec. 11, 2012

(54) SURGICAL HAND ACCESS APPARATUS

(75) Inventor: Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/307,257

(22) Filed: Nov. 30, 2011

(65) Prior Publication Data

US 2012/0136214 A1 May 31, 2012

Related U.S. Application Data

(63) Continuation of application No. 12/131,378, filed on Jun. 2, 2008, now Pat. No. 8,123,682, which is a continuation of application No. 11/101,663, filed on Apr. 5, 2005, now Pat. No. 7,393,322.

(60) Provisional application No. 60/559,678, filed on Apr. 5, 2004.

(51) Int. Cl.
*A61B 1/32* (2006.01)

(52) U.S. Cl. .................................... 606/208

(58) Field of Classification Search .......... 600/200–210, 600/190–192; 604/533–537, 248, 264, 268, 604/278, 337–339, 164.02, 164.03, 167.01–167.05; 606/108, 192, 201, 215–216

See application file for complete search history.

(56) References Cited

U.S. PATENT DOCUMENTS

| | | | |
|---|---|---|---|
| 2,305,289 A | 12/1942 | Coburg | |
| 3,332,417 A | 7/1967 | Blanford et al. | |
| 3,427,226 A | 2/1969 | McNeely | |
| 3,427,227 A | 2/1969 | Chamberlin | |
| 4,069,913 A | 1/1978 | Harrigan | |
| 4,984,564 A | 1/1991 | Yuen | |
| 5,159,921 A | 11/1992 | Hoover | |
| 5,342,385 A | 8/1994 | Norelli et al. | |
| 5,366,478 A | 11/1994 | Brinkerhoff et al. | |
| 5,368,545 A | 11/1994 | Schaller et al. | |
| 5,411,483 A | 5/1995 | Loomes et al. | |
| 5,480,410 A | 1/1996 | Cuschieri et al. | |

(Continued)

FOREIGN PATENT DOCUMENTS

DE 3737121 C2 5/1989

(Continued)

OTHER PUBLICATIONS

European Search Report for EP 09000060 dated Jun. 9, 2009. (7 pages).

*Primary Examiner* — Alvin Stewart
*Assistant Examiner* — Tara Carter

(57) ABSTRACT

A surgical access apparatus includes a liner base and an access housing for positioning outside the body. The liner base includes an inner member adapted for insertion through an opening within body tissue for positioning within the body; a sleeve member connected to the inner member and dimensioned to extend from the inner member through the opening within the body tissue, and a plurality of tensioning elements connected to the inner member and associated with the sleeve member to impart a tensioning effect on the sleeve member. The access housing includes a first element and a second element. The second element is operatively connected to the tensioning elements and adapted for rotational movement relative to the first member to cause the tensioning elements to displace the inner member toward the access housing and to cause the sleeve member to engage and retract tissue defining the opening within the body.

2 Claims, 17 Drawing Sheets

U.S. PATENT DOCUMENTS

| | | | |
|---|---|---|---|
| 5,514,133 A * | 5/1996 | Golub et al. | 606/1 |
| 5,520,610 A | 5/1996 | Giglio et al. | |
| 5,522,791 A | 6/1996 | Leyva | |
| 5,524,644 A | 6/1996 | Crook | |
| 5,526,536 A | 6/1996 | Cartmill | |
| 5,545,179 A | 8/1996 | Williamson, IV | |
| 5,634,911 A | 6/1997 | Hermann et al. | |
| 5,636,645 A | 6/1997 | Ou | |
| 5,639,937 A | 6/1997 | Hover et al. | |
| 5,640,977 A | 6/1997 | Leahy et al. | |
| 5,649,550 A | 7/1997 | Crook | |
| 5,653,705 A | 8/1997 | de la Torre et al. | |
| 5,672,168 A | 9/1997 | de la Torre et al. | |
| 5,741,298 A | 4/1998 | MacLeod | |
| 5,803,921 A | 9/1998 | Bonadio | |
| 5,810,721 A | 9/1998 | Mueller et al. | |
| 5,813,409 A | 9/1998 | Leahy et al. | |
| 5,820,600 A | 10/1998 | Carlson et al. | |
| 5,832,925 A | 11/1998 | Rothrum | |
| 5,853,395 A | 12/1998 | Crook et al. | |
| 5,899,208 A | 5/1999 | Bonadio | |
| 5,906,577 A | 5/1999 | Beane et al. | |
| 5,947,922 A | 9/1999 | MacLeod | |
| 5,957,913 A | 9/1999 | de la Torre et al. | |
| 5,964,781 A | 10/1999 | Mollenauer et al. | |
| 5,997,515 A | 12/1999 | de la Torre et al. | |
| 6,024,736 A | 2/2000 | de la Torre et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| RE36,702 E | 5/2000 | Green et al. | |
| 6,077,288 A | 6/2000 | Shimomura et al. | |
| 6,086,570 A | 7/2000 | Aboul-Hosn et al. | |
| 6,110,154 A | 8/2000 | Shimomura et al. | |
| 6,142,935 A | 11/2000 | Flom et al. | |
| 6,142,936 A | 11/2000 | Beane et al. | |
| 6,149,642 A | 11/2000 | Gerhart et al. | |
| 6,159,200 A | 12/2000 | Verdura et al. | |
| 6,162,172 A | 12/2000 | Cosgrove et al. | |
| 6,238,373 B1 | 5/2001 | de la Torre et al. | |
| 6,254,533 B1 | 7/2001 | Fadem et al. | |
| 6,254,534 B1 * | 7/2001 | Butler et al. | 600/208 |
| 6,315,770 B1 | 11/2001 | de la Torre et al. | |
| 6,319,246 B1 | 11/2001 | de la Torre et al. | |
| 6,382,211 B1 | 5/2002 | Crook | |
| 6,440,063 B1 | 8/2002 | Beane et al. | |
| 6,450,983 B1 | 9/2002 | Rambo | |
| 6,482,181 B1 | 11/2002 | Racenet et al. | |
| 6,578,577 B2 | 6/2003 | Bonadio et al. | |
| 6,610,031 B1 | 8/2003 | Chin | |
| 6,702,787 B2 | 3/2004 | Pasqualucci et al. | |
| 6,814,700 B1 | 11/2004 | Mueller et al. | |
| 6,840,951 B2 | 1/2005 | de la Torre et al. | |
| 6,846,287 B2 | 1/2005 | Bonadio et al. | |
| 6,908,430 B2 | 6/2005 | Caldwell et al. | |
| 6,942,761 B1 | 9/2005 | Prinzing et al. | |
| 7,052,454 B2 | 5/2006 | Taylor | |
| 7,393,322 B2 | 7/2008 | Wenchell | |
| 7,717,847 B2 | 5/2010 | Smith | |
| 2001/0047188 A1 | 11/2001 | Bonadio et al. | |
| 2002/0002324 A1 | 1/2002 | McManus | |
| 2002/0019609 A1 | 2/2002 | McFarlane | |
| 2002/0038077 A1 | 3/2002 | de la Torre et al. | |
| 2002/0072762 A1 | 6/2002 | Bonadio et al. | |
| 2003/0078478 A1 | 4/2003 | Bonadio et al. | |
| 2004/0015185 A1 | 1/2004 | Ewers et al. | |
| 2004/0049099 A1 | 3/2004 | Ewers et al. | |
| 2004/0092795 A1 | 5/2004 | Bonadio et al. | |
| 2004/0127772 A1 | 7/2004 | Ewers et al. | |
| 2004/0249248 A1 | 12/2004 | Bonadio et al. | |
| 2005/0020884 A1 | 1/2005 | Hart et al. | |
| 2005/0148823 A1 | 7/2005 | Vaugh et al. | |

FOREIGN PATENT DOCUMENTS

| | | |
|---|---|---|
| EP | 0 950 376 A1 | 10/1999 |
| FR | 2710270 | 9/1993 |
| GB | 2 071 502 A | 9/1981 |
| GB | 2 255 019 A | 10/1992 |
| JP | 10-108868 | 4/1998 |
| WO | WO 95/04202 | 2/1995 |
| WO | WO 95/07056 | 3/1995 |
| WO | WO 95/22289 | 8/1995 |
| WO | WO 95/27445 | 10/1995 |
| WO | WO 95/27468 | 10/1995 |
| WO | WO 96/05881 | 2/1996 |
| WO | WO 98/35614 | 8/1998 |
| WO | WO 98/48724 | 11/1998 |
| WO | WO 99/25268 | 5/1999 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 A2 | 2/2001 |
| WO | WO 01/08581 A2 | 2/2001 |

* cited by examiner

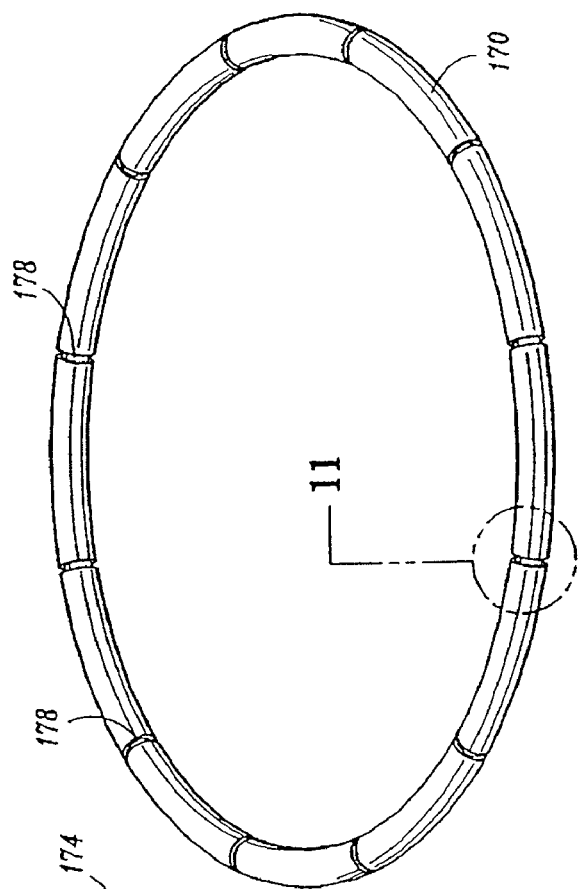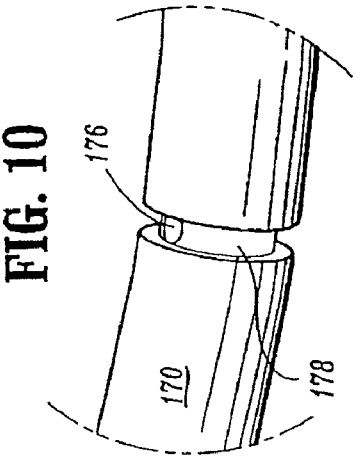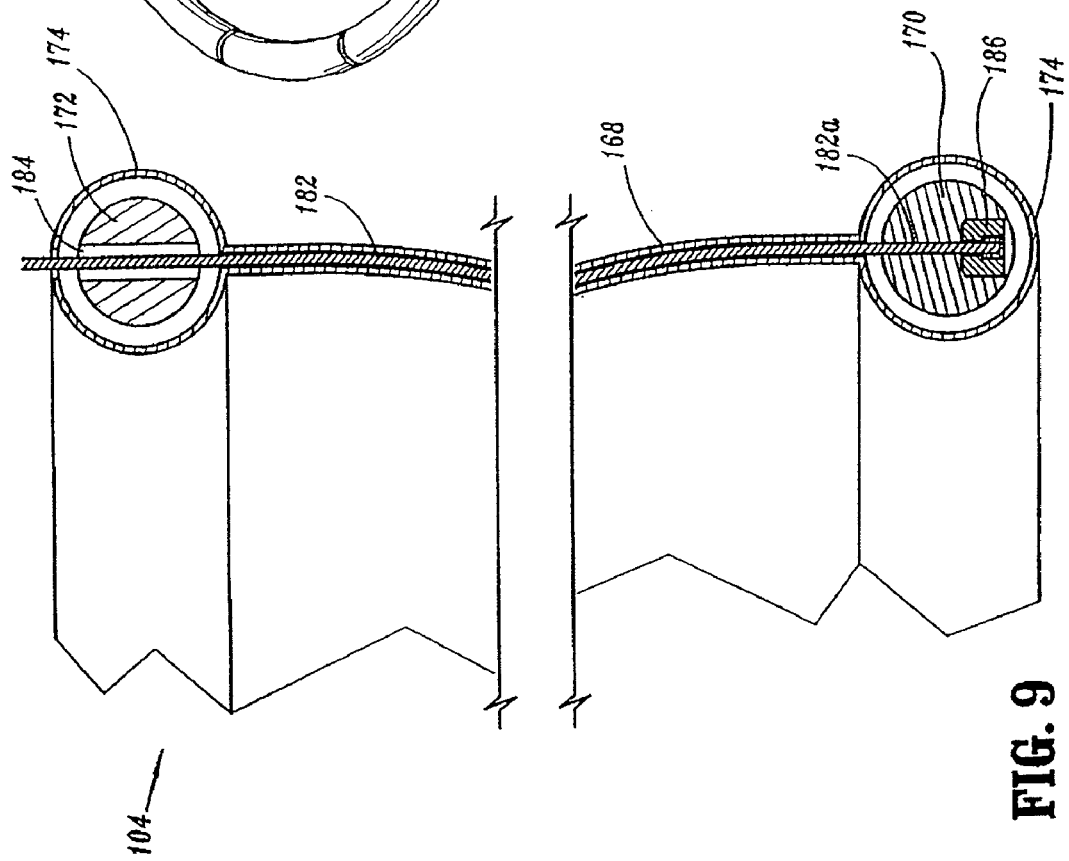

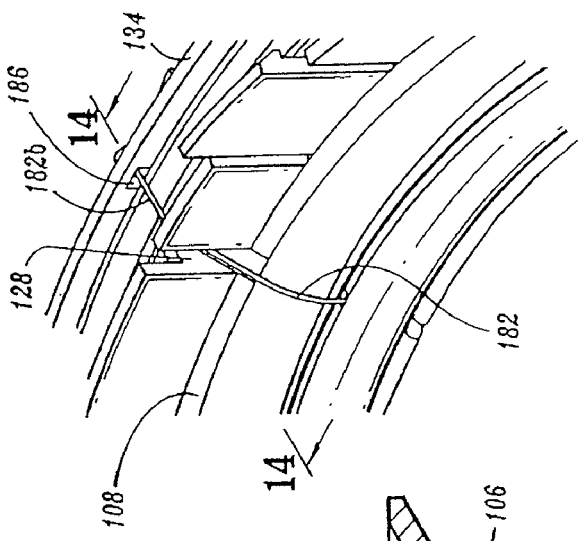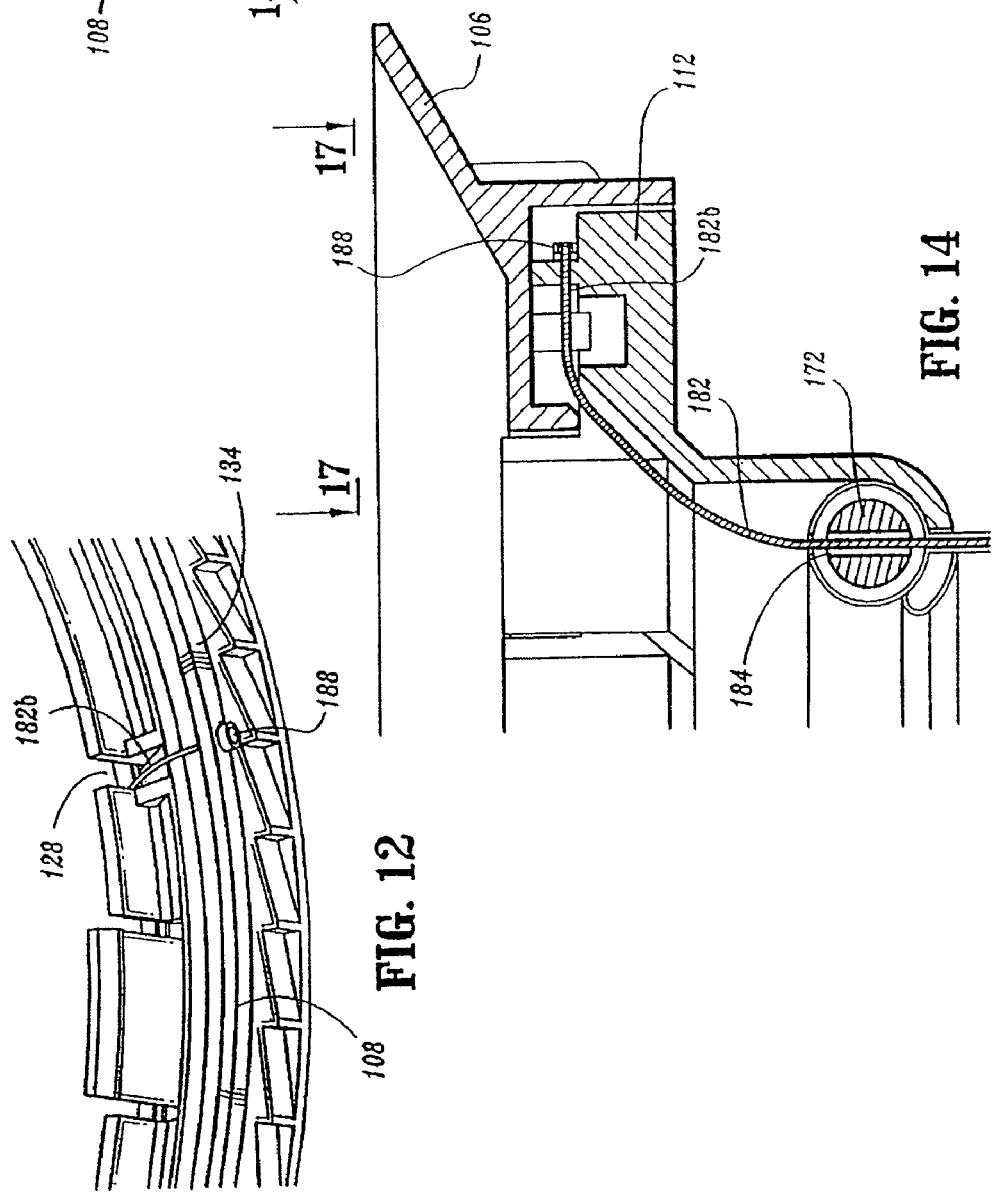

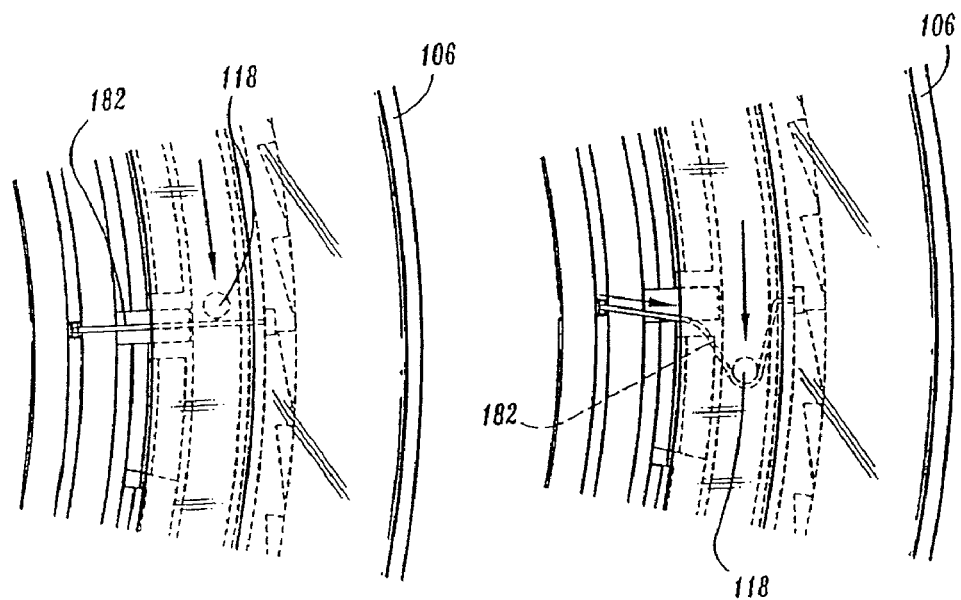
FIG. 17  FIG. 18
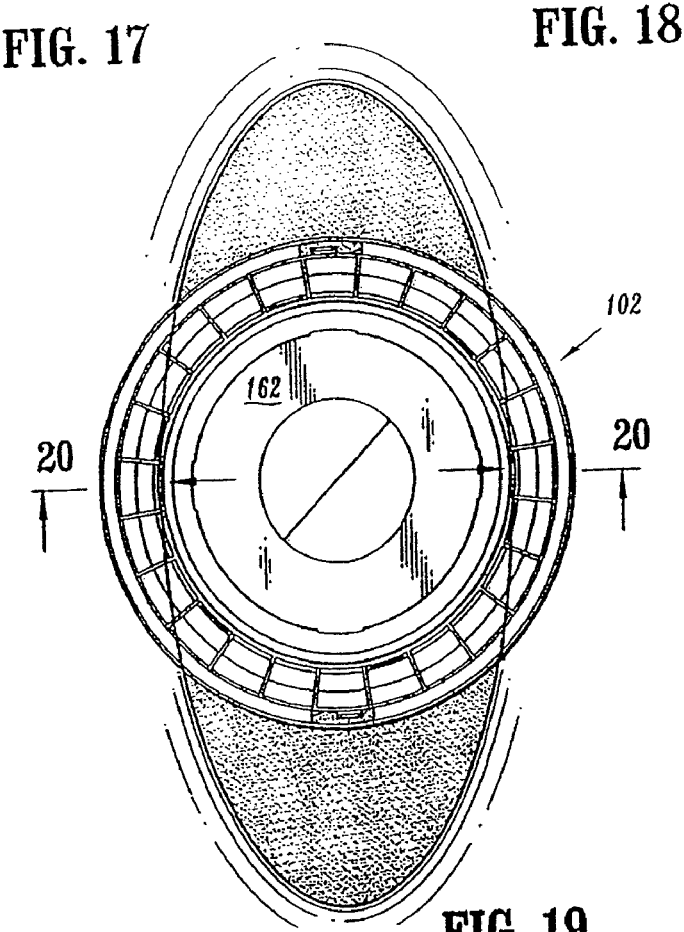
FIG. 19

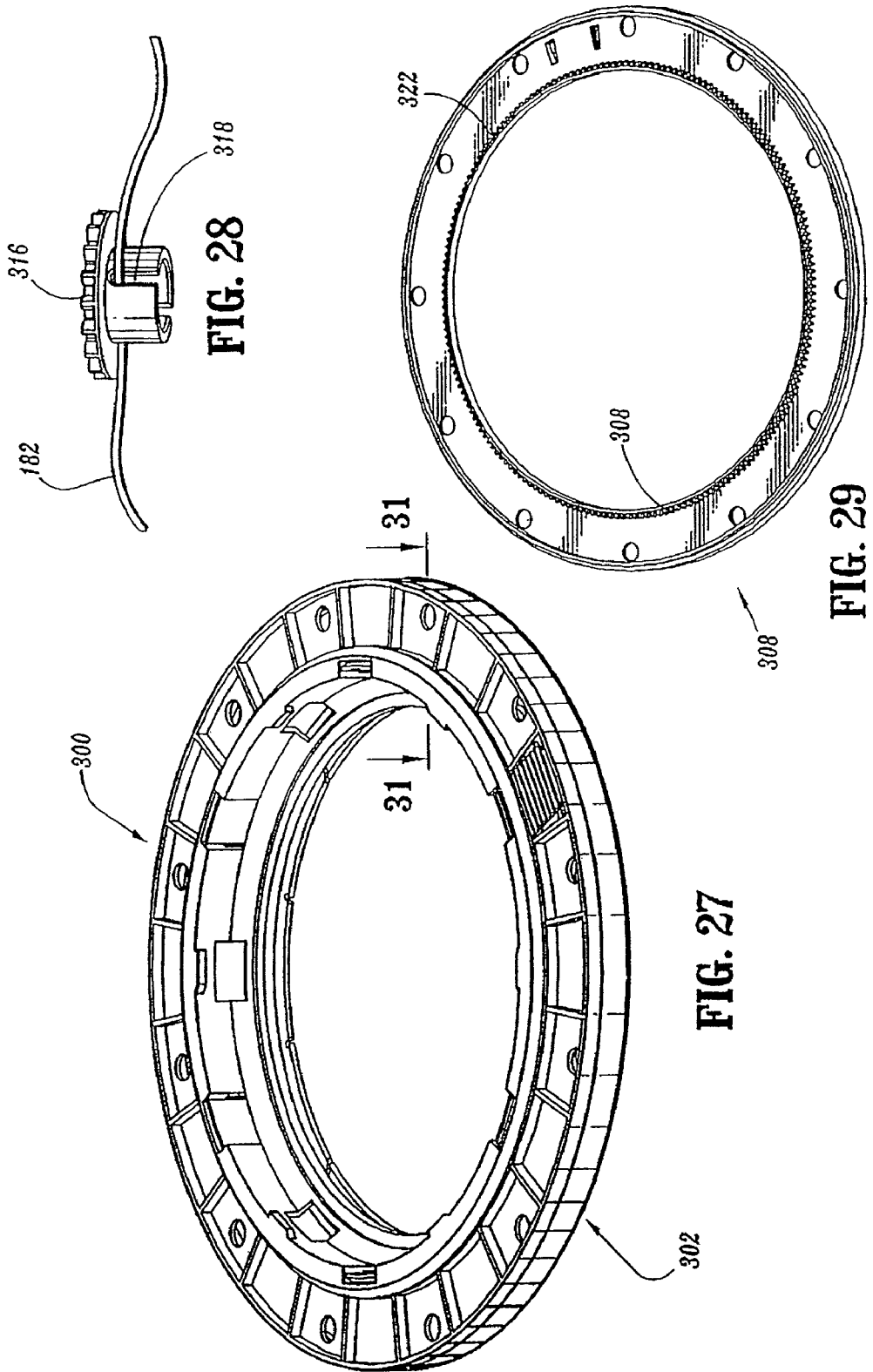

US 8,328,844 B2

SURGICAL HAND ACCESS APPARATUS

CROSS REFERENCE TO RELATED APPLICATIONS

This application is a continuation of co-pending U.S. patent application Ser. No. 12/131,378, filed on Jun. 2, 2008 now U.S. Pat. No. 8,123,682, which is a continuation of U.S. patent application Ser. No. 11/101,663, filed Apr. 5, 2005, now U.S. Pat. No. 7,393,322, which, in turn, claims the benefit of and priority to U.S. Provisional Patent Application Ser. No. 60/559,678, filed Apr. 5, 2004, now expired, the entire contents of each are incorporated herein by reference.

BACKGROUND

1. Field of the Disclosure

The present disclosure relates generally to surgical devices for facilitating sealed access across a body wall and into a body cavity and, more particularly, to a surgical access apparatus adaptable to provide selective retraction of an incision to permit the sealed insertion of either the surgeon's hand and/or surgical instruments during laparoscopic and endoscopic surgical procedures.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, e.g., in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. . . . . However, despite its recent success and overall acceptance as a preferred surgical technique, minimally invasive surgery, such as laparoscopy, has several disadvantages. In particular, surgery of this type requires a great deal of surgeon skill in order for the surgeon to manipulate the long narrow endoscopic instruments about a remote site under endoscopic visualization. In addition, in laparoscopic surgery involving the intestinal tract, it is often preferable to manipulate large sections of the intestines to perform the desired procedure. These manipulations are not practical with current laparoscopic tools and procedures accessing the abdominal cavity through a trocar or cannula.

To address these concerns, recent efforts have focused on hand-assisted laparoscopic techniques and procedures. These procedures incorporate both laparoscopic and conventional surgical methodologies. The hand assisted technique is performed in conjunction with a hand access seal which is an enlarged device positionable within the incision in, e.g., the insufflated abdominal cavity. The device includes a seal for forming a seal about the surgeon's arm upon insertion while permitting surgical manipulation of the arm within the cavity. However, known hand access seals are quite cumbersome, incorporate elaborate sealing mechanisms and are incapable of selective retraction of an incision. Moreover, these hand access seals are incapable of conversion for use with laparoscopic instruments.

SUMMARY

Accordingly, the present disclosure relates to a surgical access apparatus adaptable to permit the sealed insertion of either the surgeon's hand and/or surgical instruments during laparoscopic and endoscopic surgical procedures. In one preferred embodiment, the surgical access apparatus includes an inner member adapted for insertion through an opening within body tissue for positioning within the body, at least one tensioning element extending from the inner member and an outer member for positioning outside the body. The outer member includes a first element and a second element. The second element is operatively connected to the at least one tensioning element and adapted for rotational movement relative to the first member to cause retraction of the tissue defining the opening within the body. The at least one tensioning element is preferably connected to the inner member, and is adapted to displace the inner member toward the outer member upon rotation of the second element.

Preferably, a plurality of tensioning elements is provided. The second member is adapted to rotate relative to the first member to reduce effective lengths of the tensioning elements to displace the inner member toward the outer member into engagement with an internal body wall and to retract the tissue defining the opening. A liner member may be connected to the inner member and dimensioned to extend from the inner member through the opening within the body tissue and defining a passageway therethrough for permitting passage of an object. The tensioning elements may be embedded within the liner member and are movable relative to the liner member.

The second element of the outer member is adapted to be secured at a predetermined angular orientation relative to the first element to selectively tension the at least one tensioning element. Preferably, the second element is adapted to be secured at a plurality of predetermined angular relationships relative to the first member. Means may be provided for selectively securing the first and second elements at a plurality of relative angular relationships. One preferred means for selectively securing includes a ratchet and pawl mechanism associated with the first and second elements.

The outer member may include a seal mounted relative to the passageway of the liner member. The seal is adapted to form a fluid tight seal about an object inserted therethrough. The outer member may also include a zero closure valve mounted relative to the liner member and adapted to form a fluid tight seal in the absence of an object positioned therethrough. The zero-closure valve may be a duck bill valve.

In another preferred embodiment, the surgical access apparatus includes a liner base and an access housing for positioning outside the body. The liner base includes an inner member adapted for insertion through an opening within body tissue for positioning within the body, a sleeve member connected to the inner member and dimensioned to extend from the inner member through the opening within the body tissue, and a plurality of tensioning elements connected to the inner member and associated with the sleeve member to impart a tensioning effect on the sleeve member. The access housing includes a first element and a second element. The second element is operatively connected to the tensioning elements and adapted for rotational movement relative to the first member to cause the tensioning elements to displace the inner member toward the access housing and to cause the sleeve member to engage and retract tissue defining the opening within the body. The tensioning members are adapted to move relative to the sleeve member upon rotation of the second element and may be embedded within the sleeve member. A seal is preferably mounted to the access housing and is adapted to form a fluid tight seal about an object inserted therethrough. A zero closure valve may also be mounted relative to the liner member for forming a fluid tight seal in the absence of an object positioned therethrough. The second member of the access housing is adapted to be selectively secured at a predetermined rotational relationship with respect to the first member to provide for selective tensioning of the tensioning elements and selective retraction of tissue.

BRIEF DESCRIPTION OF THE DRAWINGS

Preferred embodiments of the present disclosure will be better appreciated by reference to the drawings wherein:

FIG. 9 is a side cross-sectional view of the liner base of the access housing illustrating the liner sleeve, upper and lower rings and the suture tensioning members;

FIG. 10 is a perspective view of the upper ring of the liner base;

FIG. 11 is an isolated view illustrating the annular grooves and suture slots within the upper ring;

FIGS. 12-13 are isolated views illustrating mounting of the suture tensioning members of the liner base to the ratchet ring;

FIG. 14 is a cross-sectional view taken along the lines 14-14 of FIG. 13 further illustrating the relationship of the tensioning members and the ratchet ring;

FIGS. 17-18 are isolated views illustrating the orientation of the suture tensioning members before and subsequent to rotation of the outer base;

FIG. 19 is a top view illustrating retraction of the incision subsequent to rotation of the outer base;

FIG. 27 is a perspective view of an alternate embodiment of the access housing of the access apparatus of FIG. 1;

FIG. 28 is a perspective view of a gear wheel of the access housing of the embodiment of FIG. 27;

FIG. 29 is a bottom view of the gear ring of the access housing of FIG. 27;

DETAILED DESCRIPTION OF THE PREFERRED EMBODIMENTS

Figure 1:
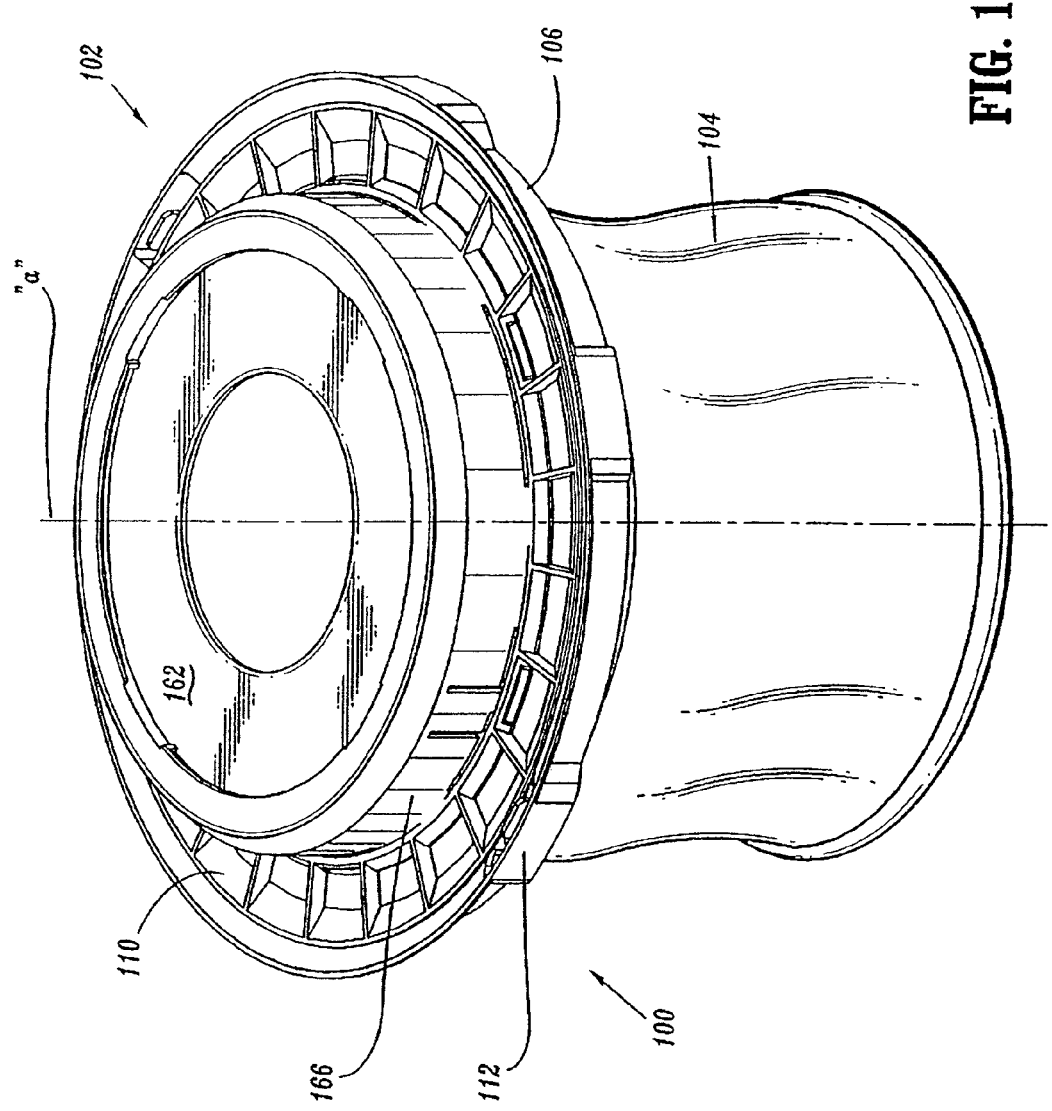
FIG. 1 is a perspective view of the hand access apparatus in accordance with the principles of the present disclosure illustrating the access housing and the liner base.

The surgical access apparatus of the present disclosure provides a substantial seal between the body cavity of a patient and the outside atmosphere before, during and after insertion of an object through the apparatus. Moreover, the access apparatus of the present invention is adapted for positioning within an incision and is capable of selectively retracting the tissue defining the incision to permit access to the underlying tissue. The access apparatus is particularly adapted for accommodating the hand and/or arm of a surgeon during a hand assisted laparoscopic procedure and establishing a gas tight seal with the arm when inserted. However, the access apparatus may be adapted to receive other objects, such as surgical instruments. The access apparatus is further adapted to substantially close in the absence of the object to maintain the integrity of the insufflated peritoneal cavity.

Although the specific focus of this disclosure will be on a preferred laparoscopic procedure, it will be noted that laparoscopic surgery is merely representative of a type of operation wherein a procedure can be performed in a body cavity with access through a body wall.

In the following description, as is traditional the term "proximal" refers to the portion of the instrument closest to the operator, while the term "distal" refers to the portion of the instrument remote from the operator.

Referring now to the drawings, in which like reference numerals identify identical or substantially similar parts throughout the several views, FIGS. 1-4 illustrate the access apparatus of the present disclosure. Access apparatus 100 generally includes two main components, namely, access housing 102 defining longitudinal axis "a" and liner base 104 which extends from the housing 102. Housing 102 includes several components which, when assembled, provide a unit which is positionable against the body of the patient. Specifically, housing 102 includes outer base 106, ratchet ring 108 disposed within the outer base 106 and ratchet hub 110. Each of outer base 106, ratchet ring 108 and ratchet hub 110 are preferably annular or ring-like in configuration defining a central aperture to permit access within housing 102.

Figure 4:
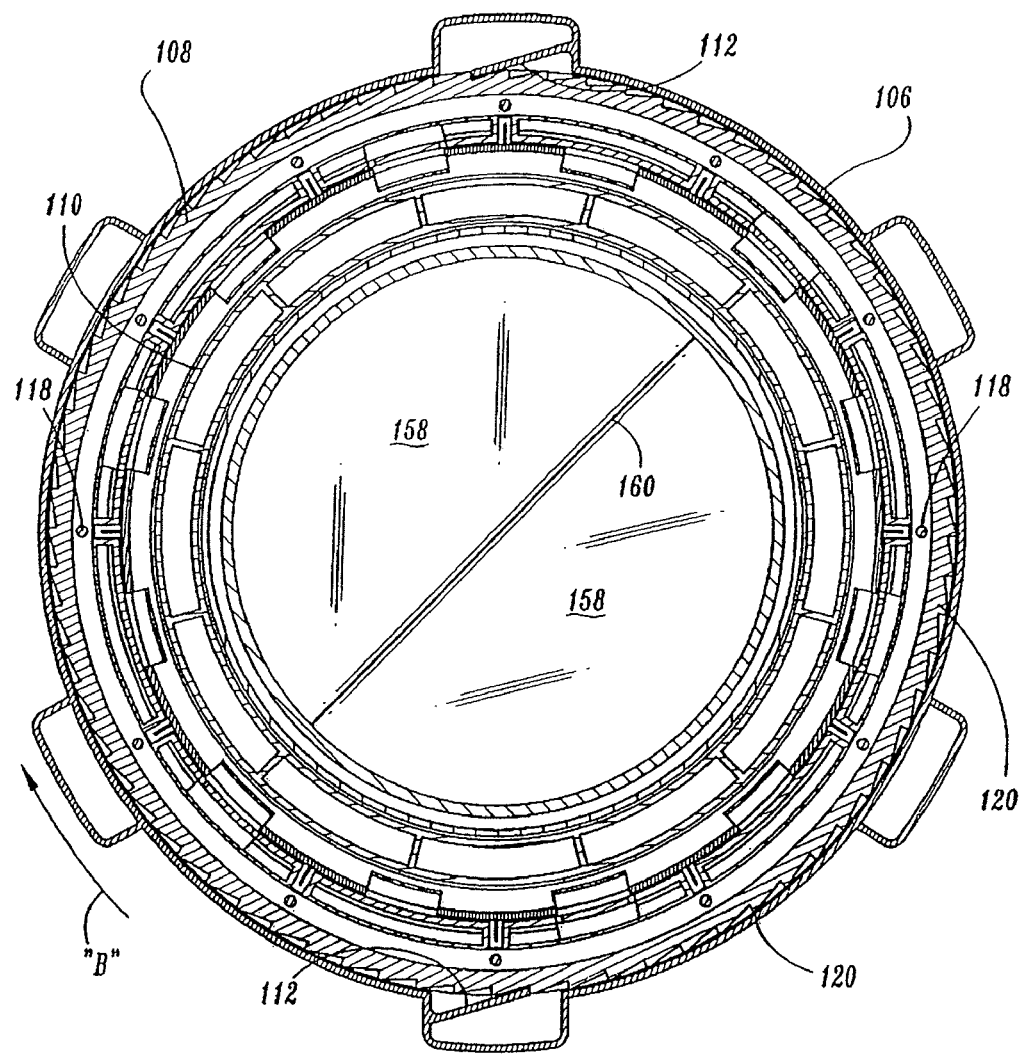
FIG. 4 is a top cross-sectional view of the access housing.
Figure 6:
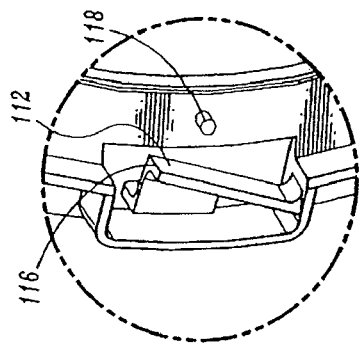
FIG. 6 is an isolated view illustrating the ratchet arm of the outer base.
Figure 5:
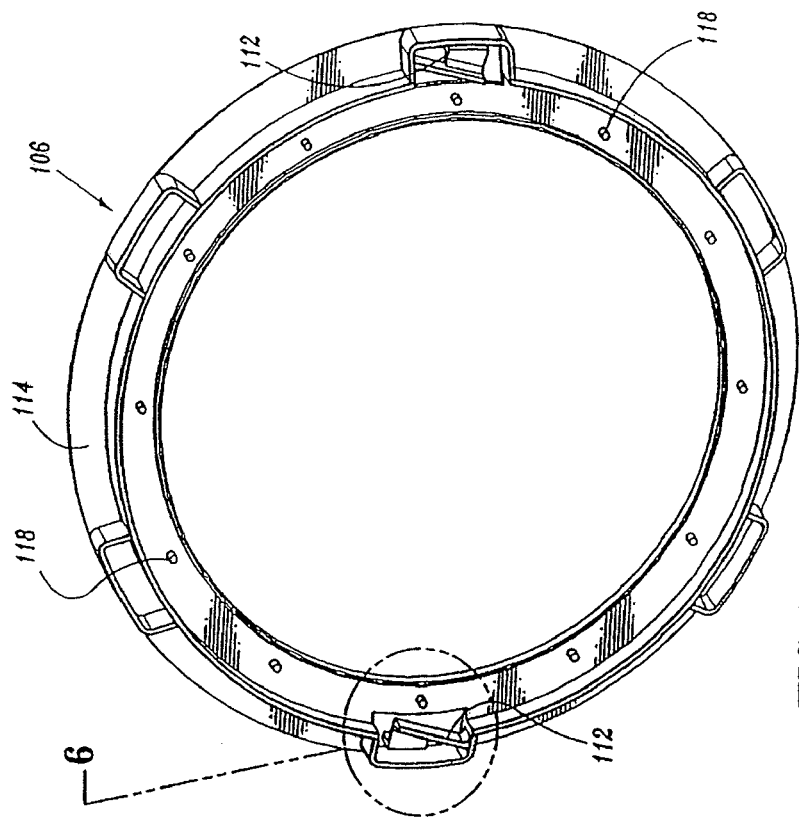
FIG. 5 is a perspective view of the outer base of the access housing.

With reference to FIGS. 5-6, in conjunction with FIGS. 1-4, outer base 106 will be discussed. Outer base 106 serves as the peripheral element enclosing the remaining components of housing 102. Outer base 106 includes a plurality (e.g., two) of ratchet arms 112 peripherally spaced adjacent its lower surface 114. Each ratchet arm 112 is spring biased radially inwardly relative to longitudinal axis "a" and defines a locking shelf 116 for engagement with components of ratchet ring 108. (See FIGS. 4-6) In one preferred arrangement, outer base 106 is monolithically formed of a plastic resilient material whereby ratchet arms 112 are normally biased inwardly but are capable of deflecting outwardly to accommodate a ratcheting action or movement of the arms 112. The lower surface 114 of outer base 102 further includes a plurality of depending contact posts 118 peripherally spaced about the surface 114. Outer base 106 is adapted for rotational movement about longitudinal axis "a" relative to ratchet ring 108 and ratchet hub 110 in the direction depicted by the directional arrow "B" in FIG. 4.

Figure 2:
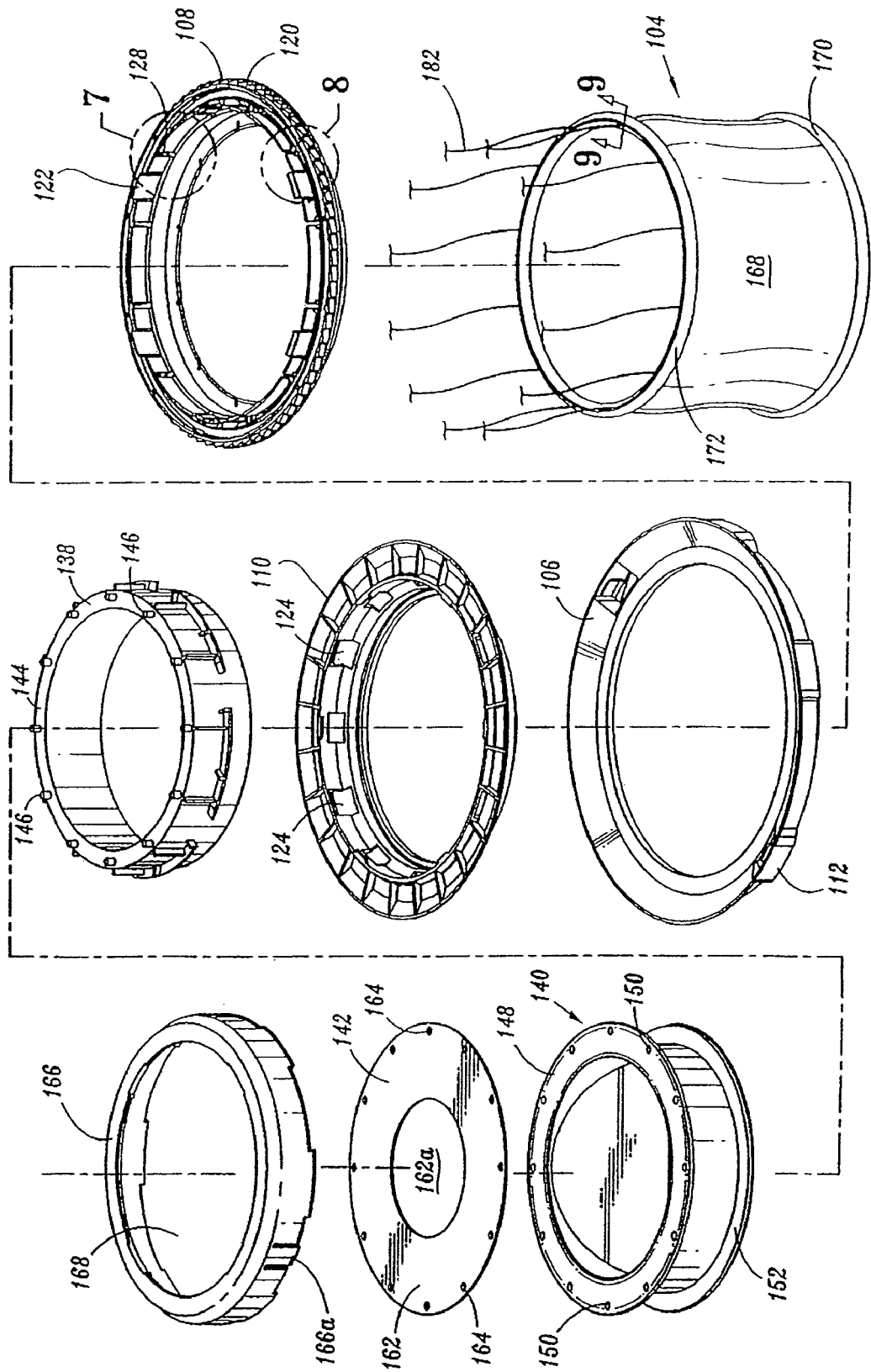
FIG. 2 is a perspective view with parts separated illustrating the components of the access apparatus in accordance with the embodiment of FIG. 1.
Figure 3:
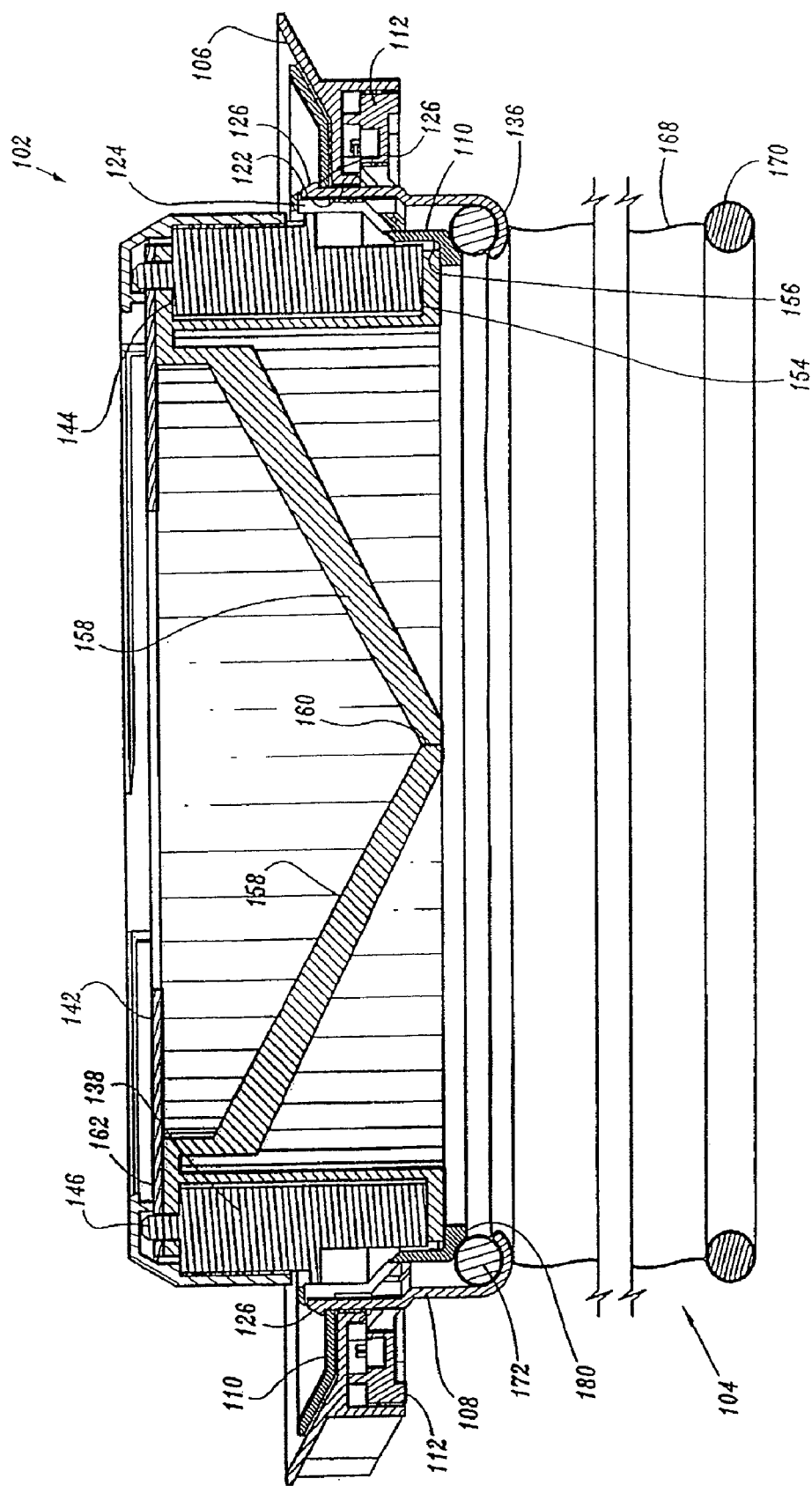
FIG. 3 is a side cross-sectional view of the access housing.
Figure 7:
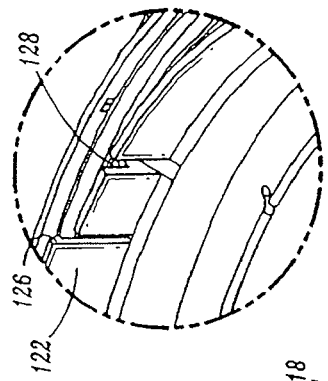
FIG. 7 is an isolated view illustrating the suture receiving slots of the ratchet ring of the access housing.
Figure 8:
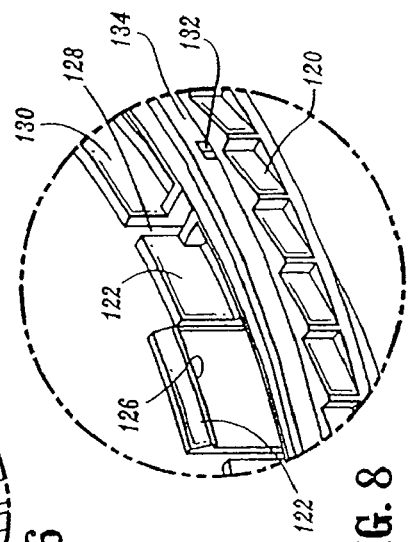
FIG. 8 is an isolated view illustrating the ratchet teeth of the ratchet ring of the access housing.

Referring now to FIGS. 7-8, in view of FIGS. 2-4, ratchet ring 108 and ratchet hub 110 are disposed around a lower end of the outer bass 106. Ratchet ring 108 includes a plurality of external ratchet teeth 120 which cooperate with ratchet arms 112 of outer base 106 to selectively lock the relative position of outer base 106 and ratchet ring 108. Ratchet ring 108 further includes a plurality of upwardly extending tabs 122 (FIGS. 2 and 7) which are received within correspondingly positioned apertures 124 (FIG. 2) of ratchet hub 110. Tabs 122 may include locking shelves 126 which engage ratchet hub 110 to secure the ratchet ring 108 and ratchet hub 110. In alternative embodiments, the ratchet ring 108 and ratchet hub 110 are integrally formed in a single structured. In a preferred embodiment, ratchet ring 108 and ratchet hub 110 are stationary. Ratchet ring 108 further includes a plurality of slots 128 within inner peripheral wall 130 and aperture 132 in outer peripheral wall 134. Ratchet ring 108 further defines u-shape trough 136 (FIG. 3) which contacts the skin of the patient during use.

Referring again to FIGS. 1-4, access housing 102 further includes valve support 138, duck bill valve 140 and septum seal 142. Valve support 138 is an elongated annular collar which extends within outer base 106. The upper surface 144 of valve support 138 defines a plurality of upwardly extending posts 146 peripherally spaced about the upper surface 144. Duck bill valve 140 is mounted to valve support 138. The duckbill valve 140 preferably comprises an elastomeric material. Specifically, duck bill valve 140 includes circumferential flange 148 having a plurality of apertures 150. Apertures 150 are dimensioned to receive correspondingly positioned posts 146 of valve support 138 to fix the valve 140 relative to the valve support 138. Duck bill valve 140 further includes lower or distal flange 152 which is positioned between the lower surface 154 of the valve support 138 and an interior ledge 156 of ratchet hub 110. (FIG. 3) Duck bill valve 140 defines a pair of interior walls 158 obliquely arranged relative to the longitudinal axis and terminating in adjacent relation to define a slit 160. Slit 160 opens to permit passage of an object by deflection of walls 158 and closes in the absence of the object as facilitated by the pressure of insufflation gases within the cavity, i.e., duck bill seal is a zero-closure seal. Alternatively, other zero closure seals may also be incorporated within apparatus 100.

With continued reference to FIGS. 1-4, septum seal 142 is positioned adjacent duck bill valve 140. Septum seal 142 includes a peripheral seal area 162 surrounding central aperture 162a. Peripheral area 162 includes a plurality of openings 164 which receive the upper ends of posts 146 of valve support 112 to fix the septum seal 142 within housing 102. Seal 142 is adapted to form a substantial seal about an object inserted through aperture 162a and may stretch to accommodate larger size objects. Septum seal 142 is preferably formed of an elastomeric material. Although described as a septum seal, it is appreciated that seal 142 could be a slit valve, balloon valve, gel seal or any other seal available in the art. In one embodiment, seal 142 preferably comprises a gel material such as a soft urethane gel, silicon gel, etc. and preferably has compressible characteristics to permit the seal 142 to conform and form a seal about the outer surface of a surgeon's hand and/or arm during insertion and manipulation about the operation site.

In an alternate preferred embodiment, seal 142 is fabricated from a resilient material, e.g., polyisoprene, and has at least one layer of fabric material positioned adjacent the resilient material. The seal 142 may be fabricated from an elastomeric material molded with a fabric manual. A friction resisting coating may be applied to seal 142. This seal is disclosed in commonly-assigned U.S. patent application Ser. No. 10/165,373 filed Jun. 6, 2002, the contents of which are incorporated in its entirety by reference. Other valve types are also contemplated including zero-closure valves, septum valves, slit valves, double-slit valves, inflatable bladders, other foam or gel valve arrangements, etc.

With continued reference to FIGS. 1-4, housing 102 further includes cover 166 which is positioned over septum seal 142 to substantially enclose valve support 138, duck bill valve 140 and septum seal 142. Cover 166 includes an aperture 168 to permit access to the interior of housing 102. Preferably, cover 166 incorporates structure to engage a corresponding surface or structure of ratchet ring 108 or ratchet hub 110 to secure the cover 166 within housing 102. For example, cover 166 may include a plurality of tabs 166a on its exterior surface which lock into corresponding recesses within ratchet ring 108 or ratchet hub 110. Other means for connecting cover 102 within housing 102 are also envisioned. The cover 166, outer base 106, ratchet ring 108 and ratchet hub 110 are desirably formed from a relatively rigid polymeric material such as polycarbonate.

Referring now to FIGS. 1-3 and 9-11, liner base 104 will be discussed. Liner base 104 is intended for positioning within the incision of the patient to line the incision and/or retract the tissue defining the incision thereby enhancing access to the underlying body cavity. Liner base 104 includes sleeve 168, lower ring 170 and upper ring 172 connected to respective ends of the sleeve 168. Sleeve 168 may be a sheet of flexible material including, for example, polyethylene, polypropylene, etc., arranged in a tubular configuration. Preferably, sleeve 168 is double walled as shown in FIG. 9 and defines enlarged ring-like areas 174 to accommodate lower and upper rings 170, 172. Sleeve 168 may also include an elastomeric material. Although in the preferred embodiment, sleeve 168 is tubular, it is envisioned that the sleeve 168 may incorporate several pieces, e.g., individual tabs or the like. Sleeve 168 may or may not be impervious to fluids, but preferably protects an incision through tissue from contamination.

Lower ring 170 is adapted for positioning through the incision and beneath the abdominal wall to engage the interior wall portions to thereby secure sleeve 168 relative to the incision. Lower ring 170 is preferably flexible to facilitate passage through the incision and possesses sufficient resiliency to return to its original configuration upon entering the abdominal cavity. Lower ring 170 includes a plurality of longitudinal openings 176 and annular grooves 178 as depicted in FIGS. 10 and 11. Grooves 178 facilitate collapsing of lower ring 170 upon itself when passing through the incision. In alternative embodiments, the ring 170 may be flexible enough to deform while being inserted through an incision, without incorporating grooves 178. Lower ring 178 is preferably annular or ring-like in configuration and may be fabricated from an elastomeric material. Lower ring 170 is accommodated within the enlarged ring-like area 174 of sleeve 168.

Referring now to FIGS. 2 and 9, upper ring 172 of liner base 104 is substantially identical in configuration to lower ring 170. As best depicted in FIG. 3, upper ring 172 is accommodated within the enlarged ring-like area 174 of sleeve 168. In the assembled condition, upper ring 172 is received within u-shape trough 136 of ratchet ring 108 and is secured between the trough 136 and lower surface 180 of ratchet hub 110 (FIG. 3).

Liner base 104 further includes a plurality of tensioning members 182 which extend within the doubled wall of sleeve 168. Tensioning members 182 are secured to lower ring 170 and extend out from sleeve 168 through openings 184 provided in upper ring 172. Tensioning members 182 may comprise strings, tabs or the like, including sutures. In one embodiment, the ends 182a of tensioning members 182 are secured within lower ring 170 with suture ferrules 186. Other means to connect the suture ends 182a to lower ring 170 are also envisioned. Tensioning members 182 move within sleeve 168 upon rotation of outer base 106 of access housing 102 to displace lower ring 170 toward upper ring 172 and access housing 102.

As depicted in FIGS. 12-14, the outer ends 182b of tensioning members 180 are accommodated within receiving slots 128 of ratchet ring 108 and extend through openings 186 of outer wall 134 of the ratchet ring 108. Tensioning members 182 are secured within openings 186 of ratchet ring 108 by conventional means including with the use of suture ferrules 188, or anchors, knots, etc. Tensioning members 182 are adapted to slide within sleeve 168 upon rotation of outer base 106 to displace lower ring 170 toward upper ring 172 so as to bring the lower ring 170 into engagement with the inner body wall. By rotation of outer base 106, the effective lengths of tensioning members 182 are reduced. Such motion also imparts a tensioning and retracting effect on sleeve 168 to cause the sleeve 168 to engage and retract tissue defining the incision. Tensioning members 182 may be any suitable flexible member including sutures, cables, drawstrings or the like.

In further embodiment, the sleeve incorporates tensioning members in a wall of the sleeve or extending from an upper end of the sleeve so that the tensioning members and sleeve are integral with one another.

Operation

Figure 15:
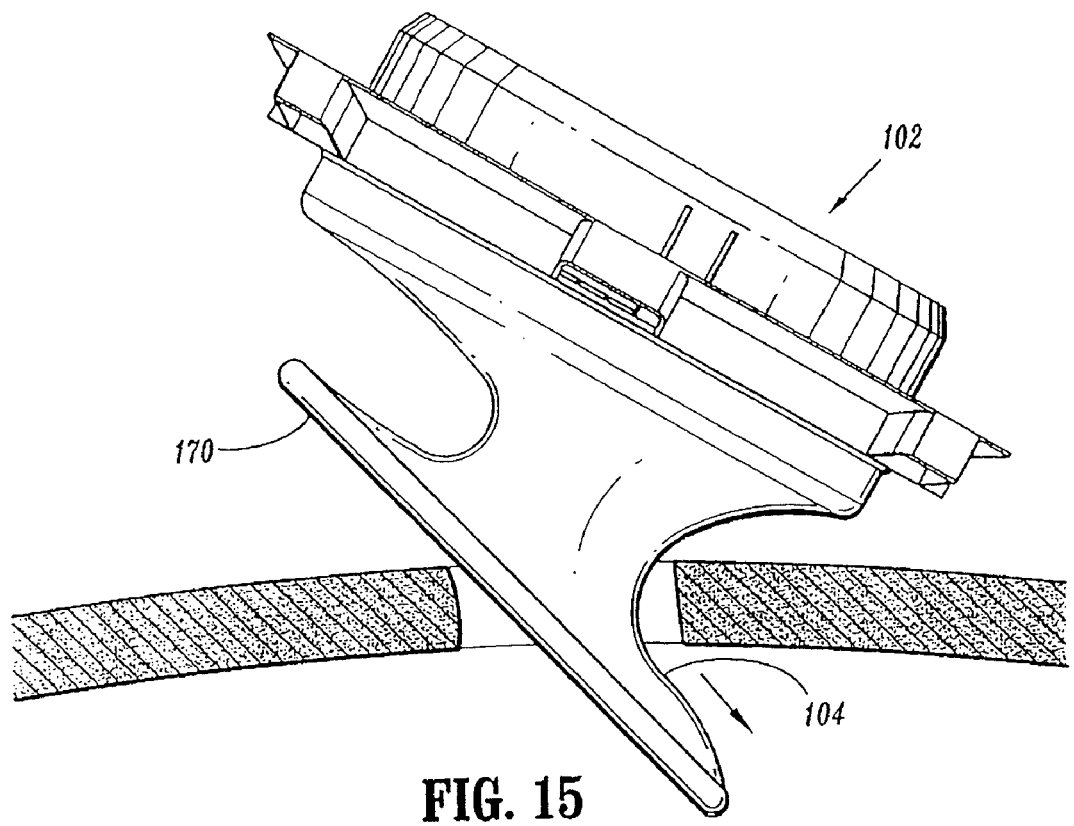
FIGS. 15-16 are views illustrating positioning of the hand access apparatus of FIG. 1 within an incision.
Figure 16:
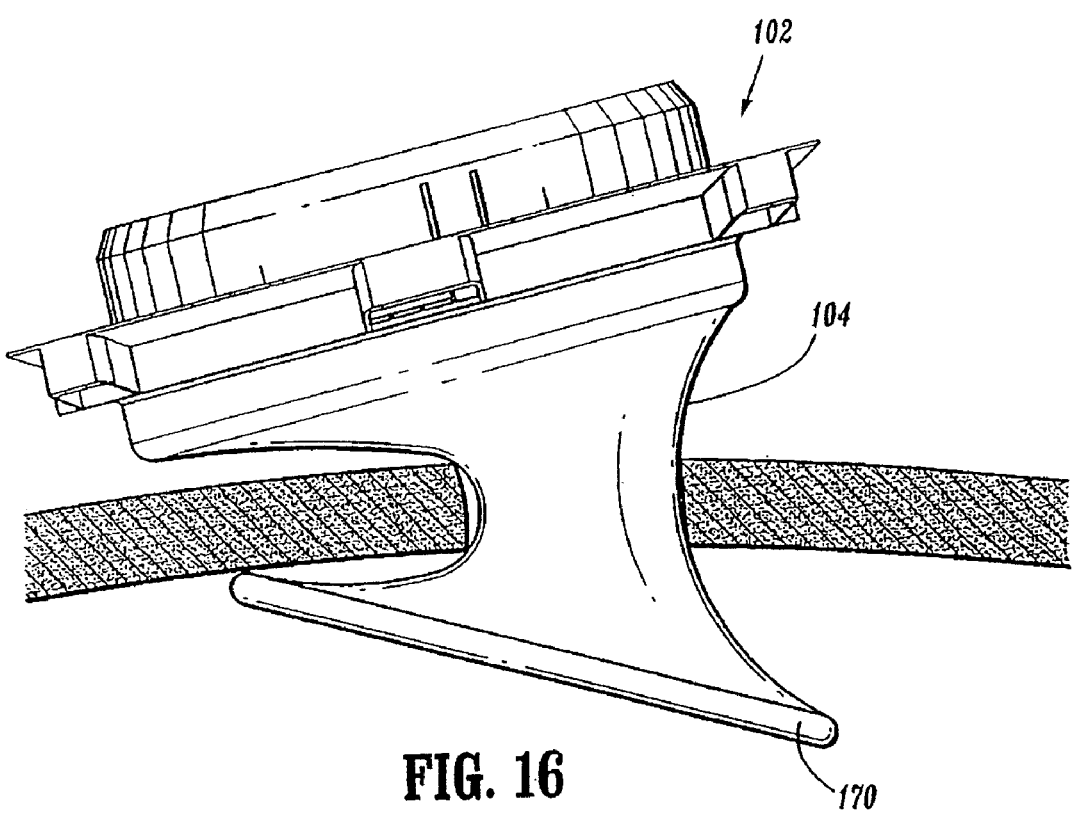

The use of the access apparatus 100 in connection with a hand assisted laparoscopic surgical procedure will be discussed. The peritoneal cavity is insufflated and an incision is made within the cavity, with e.g., a trocar, to provide access to the cavity as is conventional in the art. Thereafter, as depicted in FIGS. 15-16, liner base 104 is introduced within the incision. Specifically, lower ring 170 is passed through the incision and placed within the body cavity. As noted, lower ring 170 may be contracted upon itself to facilitate passage through the incision and then released to permit the lower ring 170 to return to its normal condition (under the influences of its inherent resiliency) within the cavity. Liner sleeve 168 extends from lower ring 170 through the incision to line the incision as previously discussed.

Figure 20:
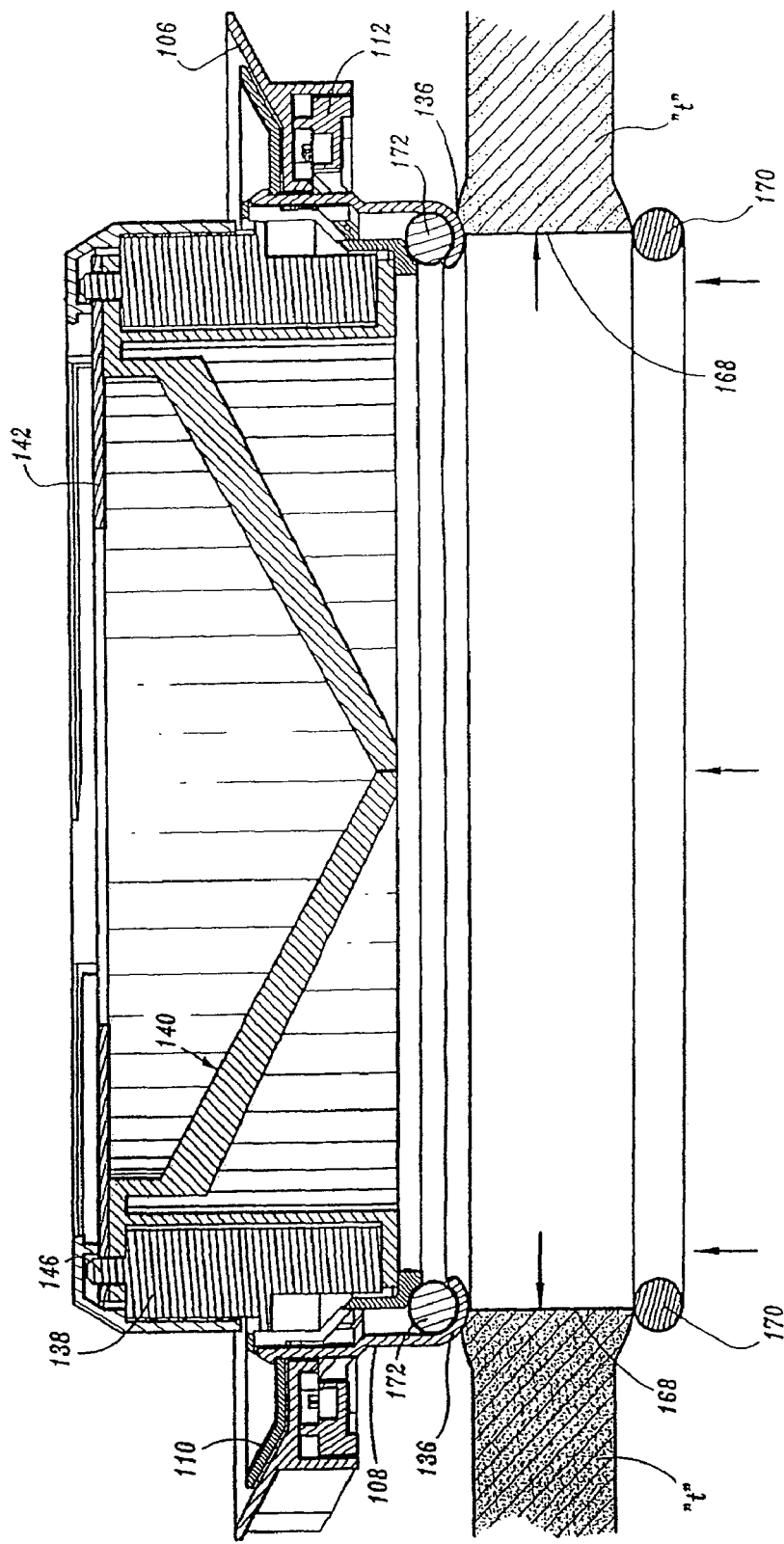
FIG. 20 is a side cross-sectional view similar to the view of FIG. 3 further illustrating retraction of the incision.

The procedure is continued by positioning access housing 102 adjacent the external body tissue with the outer surface of trough 136 of ratchet ring 108 engaging the tissue surrounding the incision. Thereafter, when it comes desirable to increase the size of the incision, outer base 106 is rotated in the direction of directional arrow "B" of FIG. 4. As outer base 106 rotates, engaging posts 118 of outer base 106 engage tensioning members 182 to deflect the tensioning members 182 from the arrangement shown in FIG. 17 to the arrangement shown in FIG. 18. During this movement, the tensioning members 182 draw lower ring 170 of liner base 104 toward upper ring 172. Simultaneously, a tensioning effect is imparted to sleeve 168 which causes the sleeve 168 to retract tissue. As appreciated, the amount of deflection of tensioning members 182 through rotation of outer base 106 is selectively controllable through the associated ratchet mechanism. In addition, the sleeve 168 is tensioned and the tissue is retracted without requiring the surgeon to pull on or otherwise arrange the sleeve 168. Outer base 106 may be rotated relative to ratchet ring 108 sufficiently to draw the lower ring 170 of liner base 104 into engagement with the interior wall of the body cavity. FIG. 20 illustrates lower ring 170 engaged with the inner wall of the body cavity with sleeve 168 retracting tissue "t" defining the incision.

Figure 21:
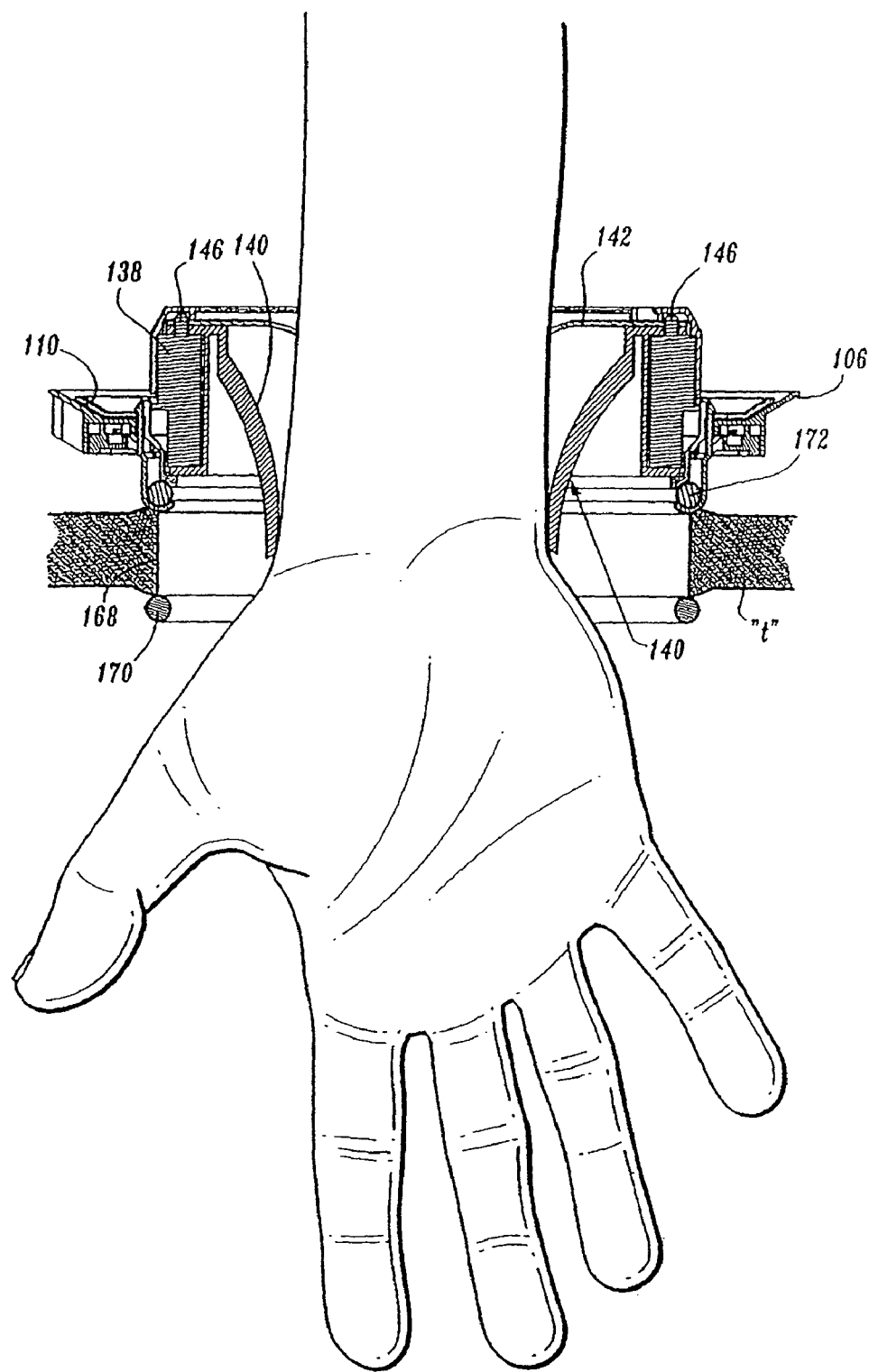
FIG. 21 is a view illustrating insertion of a hand through the access apparatus.

With access apparatus 100 in this position of FIG. 20, hand assisted surgery may then be effected by advancement of the surgeon's hand and arm through seals 142, 140 of access housing 102 and into the body cavity (FIG. 21). Seal 142 forms a fluid tight seal about the arm. The desired hand assisted procedure may then be performed.

Figure 23:
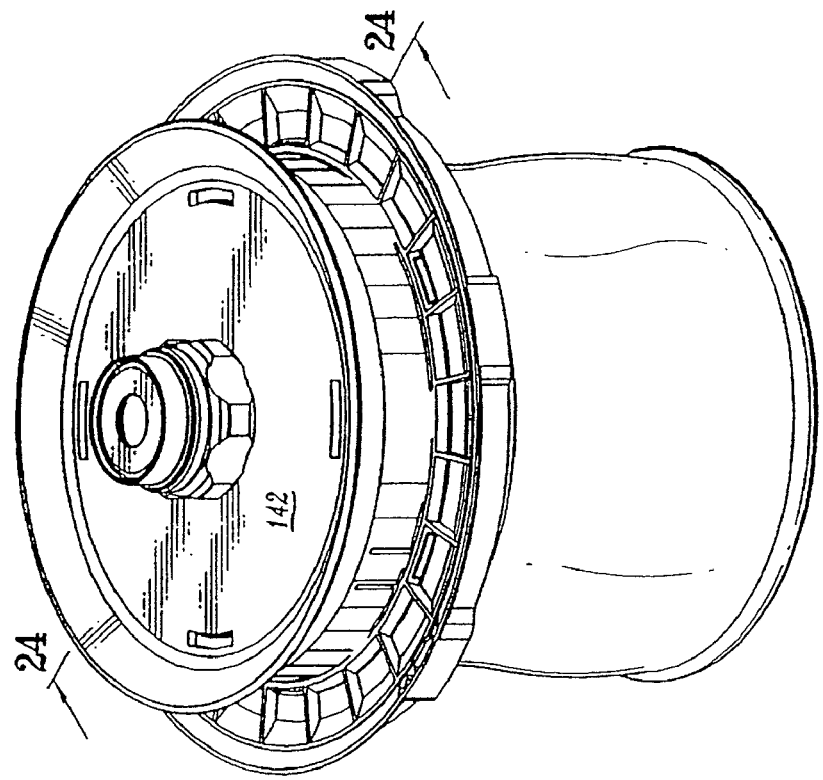
FIGS. 22-23 are perspective views of a trocar adapter for use with the access apparatus in accordance with the embodiment of FIG. 1.
Figure 22:
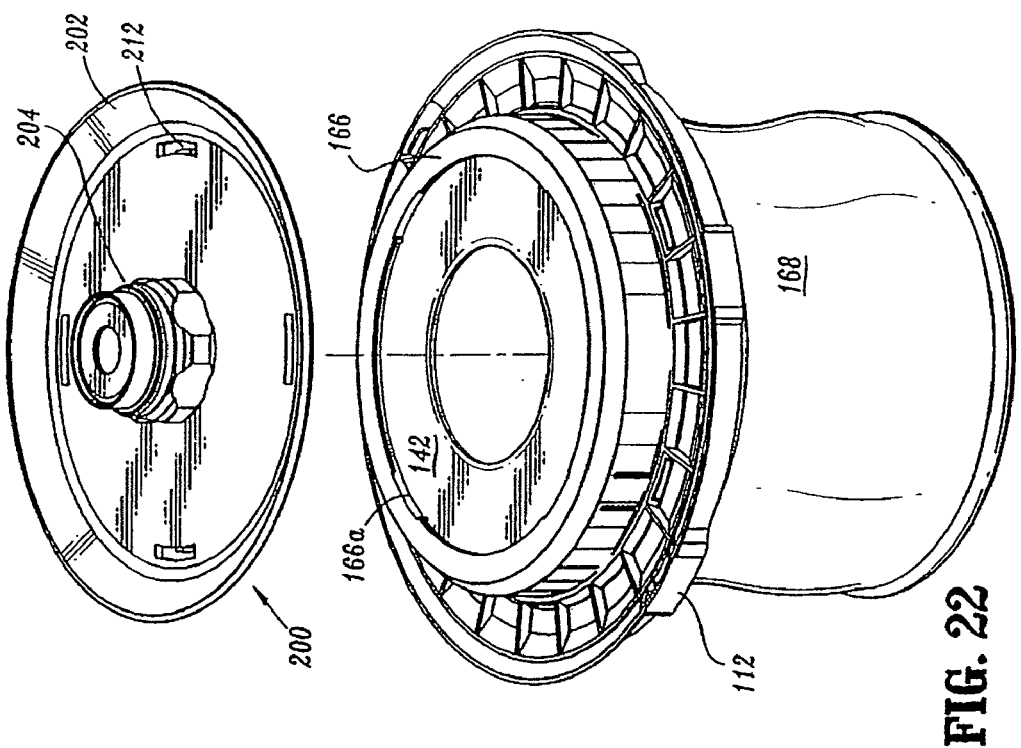
Figure 24:
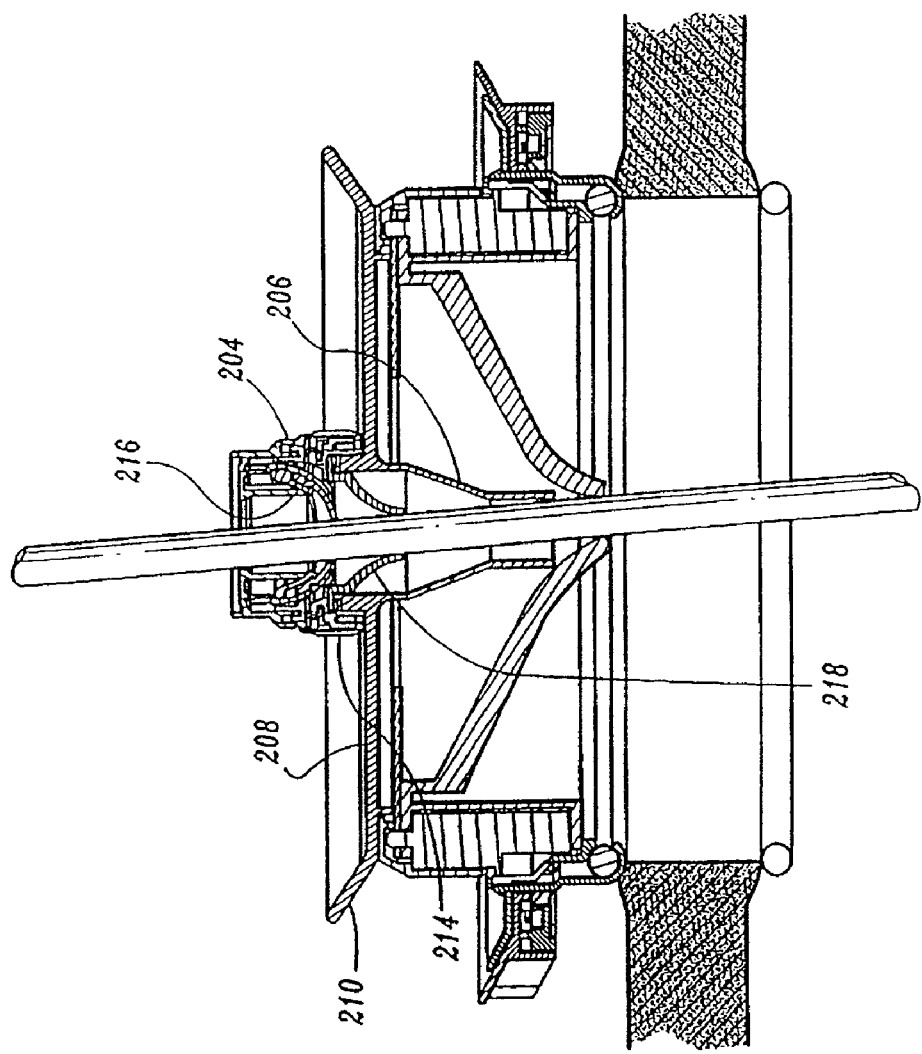
FIG. 24 is a side cross-sectioned view taken along the lines 24-24 of FIG. 23.

One other salient feature of access apparatus 100 is the ability to convert hand access apparatus 100 for use with laparoscopic instrumentation. In this regard, and with reference to FIGS. 22-24, a trocar adapter 200 is provided. Trocar adapter 200 includes adapter base 202 and valve assembly 204 which is mounted to the adapter base 202. Adapter base 202 includes trocar sleeve 206, inner wall 208 extending from the sleeve 206 and peripheral flange 210. Trocar sleeve 206 is a tube-like structure having a longitudinal opening defining an internal dimension suitable for passage of surgical instrumentation. The proximal end of trocar sleeve 206 extends beyond inner wall 208 for attachment to valve assembly 204. Adapter base 202 is preferably monolithically formed as a single unit and may be fabricated from a suitable polymeric material through injection molding techniques. Alternatively, adapter base 202 may be formed of a suitable biocompatible metal material like stainless steel, titanium, titanium alloys etc.

Adapter base 202 is preferably releasably mounted to access housing 102. In one preferred arrangement, adapter base 202 includes peripheral tabs 212 depending from its lower surface which engage recesses 166a of cover 166 to secure the base 202 to the cover. Other means for releasably connecting adapter base 202 to access housing 102 are also envisioned including a bayonet coupling, friction fit, tongue and groove, etc. Adapter base 202 may also be tethered to access housing 102 to provide a flip-top arrangement.

Valve assembly 204 may be any conventional trocar seal system adapted for mounting to a trocar sleeve and forming a fluid tight seal about an endoscopic instrument ranging in diameter from about 3 mm to about 15 mm. In one preferred embodiment, valve assembly 204 is of the type available from United States Surgical Corporation of Norwalk, Conn. under the tradename, VERSAPORTPLUS™. The VERSAPORT-PLUS™ seal includes a valve housing 214, a gimbal valve 216 mounted within the housing and a zero-closure or duckbill valve 218 extending from the valve housing 214 and into trocar sleeve 206. Gimbal valve 216 is adapted to swivel or rotate within valve housing 214 about a central axis of rotation to accommodate offset manipulation of the instrument inserted through valve assembly 204. Duck bill valve 218 is adapted to open in the presence of an instrument and close to function as a zero closure seal in the absence of an instrument. Valve housing 214 is connected to the proximal end of trocar sleeve 200 through any conventional means including adhesives, bayonet coupling, etc. Other valve assemblies for incorporation into adapter 200 are also envisioned such as the valve assemblies disclosed in commonly assigned U.S. Pat. Nos. 6,482,181, 5,820,600, RE 36,702 and application Ser. No. 09/706,643, filed Nov. 6, 2000, the entire contents of each being incorporated by reference. Once mounted, trocar sleeve 206 extends through aperture 162a of seal 142. Seal 142 forms a fluid-tight seal about the outer surface of trocar sleeve 206. Instrumentation is introduced through valve assembly 204 and trocar sleeve 206 to carry out the desired procedures. As mentioned, gimbal valve 216 of valve assembly 204 forms a fluid tight seal about the instrument and permits manipulation of the instrument within the operative site.

Figure 25:
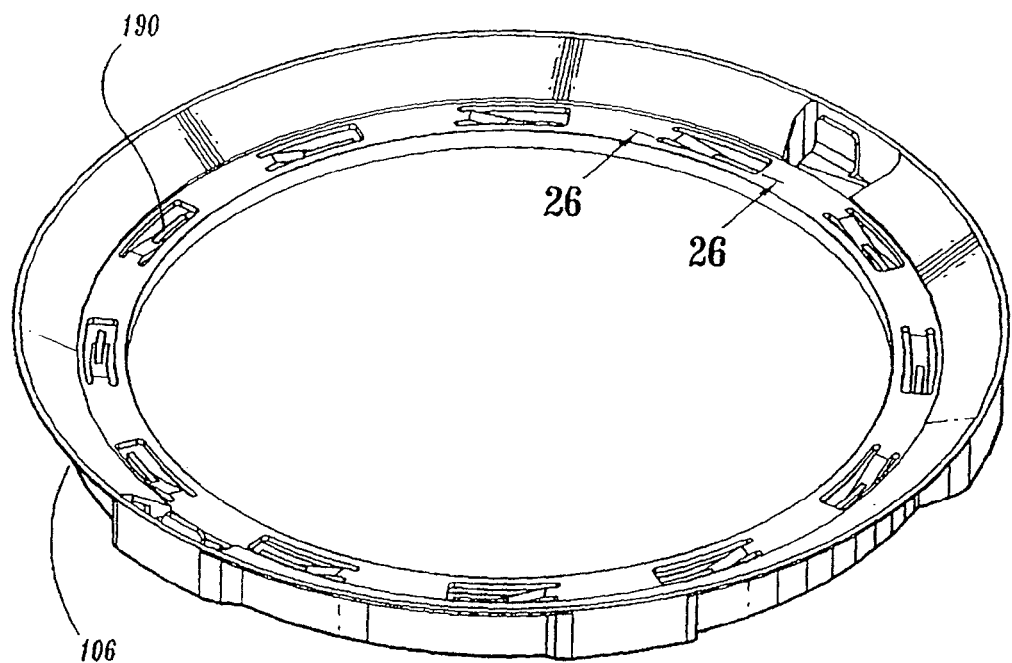
FIG. 25 is a perspective view of an alternate embodiment of the outer base of the access housing.
Figure 26:
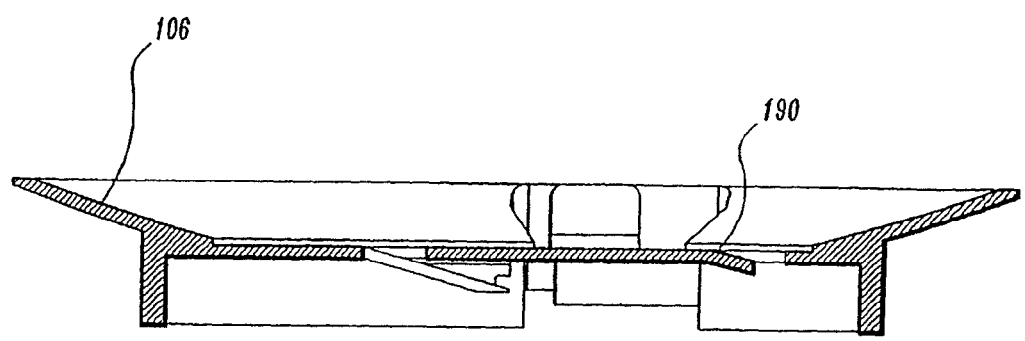
FIG. 26 is a cross-sectional view taken along the lines 26-26 of FIG. 25 illustrating the suture forks of the outer base of the embodiment of FIG. 25.
Figure 30:
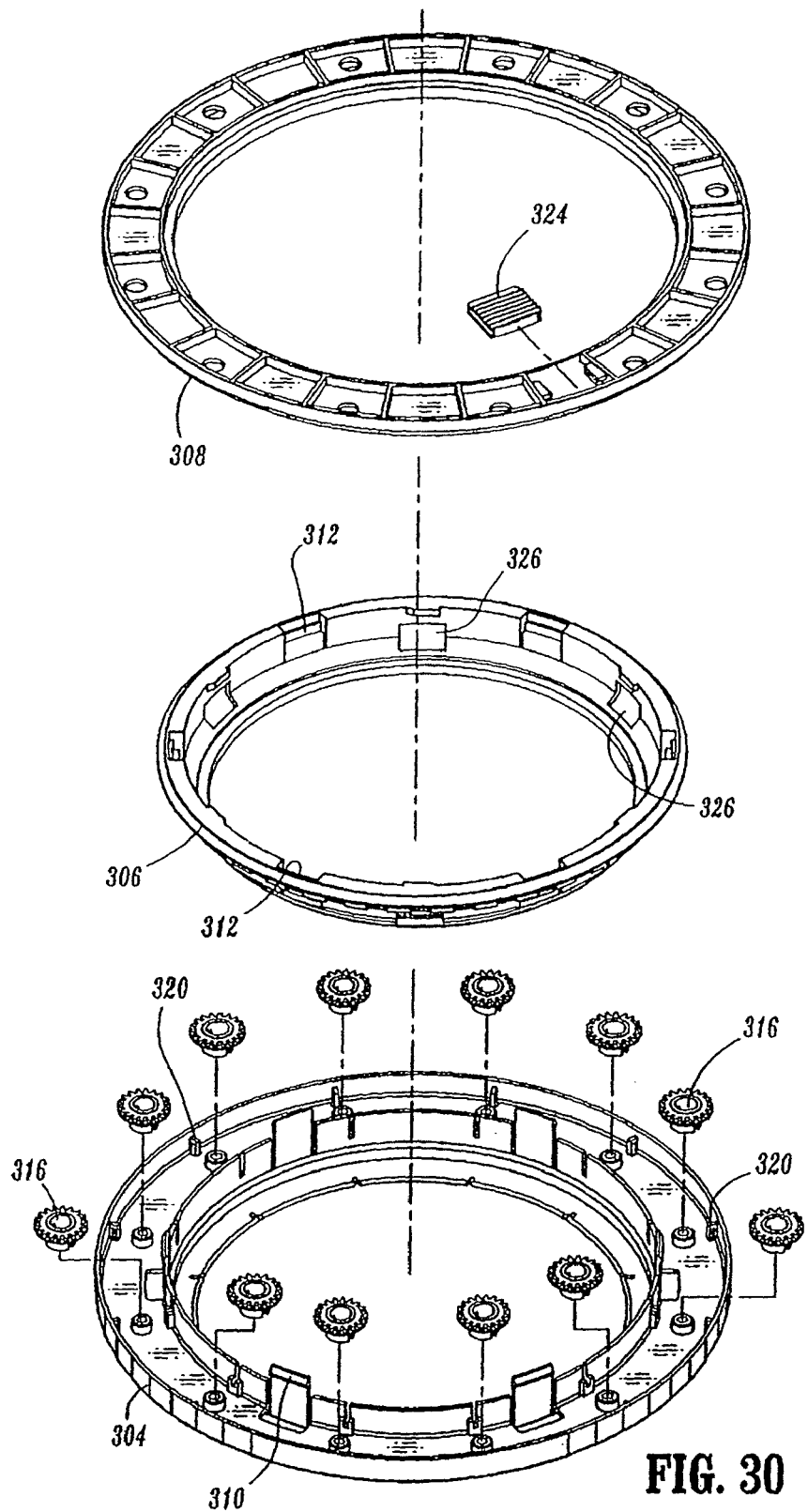
FIG. 30 is a perspective view with parts separated of the access housing of FIG. 27.

FIGS. 25-26 illustrate an alternate embodiment of the outer base 106 of access housing 102. In accordance with this embodiment, the contact posts 118 which engage tensioning members 182 during rotation of the outer base 106 are replaced with forks 190. Forks 190 depend downwardly from the lower suture of outer base 106 at an oblique angle and capture the tensioning members 182 during rotation of outer base 106. In all other regards, access apparatus 100 operates in the same manner as that described in connection with the embodiment of FIG. 1.

FIGS. 27-32 illustrate another alternate embodiment of the present disclosure. In accordance with this embodiment, access apparatus 300 includes access housing 302 having wheel mount 304, wheel hub 306 mounted to the wheel mount 304 and gear ring 308. Wheel mount 304 and hub 306 are secured to each other through corresponding engagement of tabs 310 of the wheel mount 304 and slots 312 of the wheel hub 306. Wheel mount 304 and wheel hub 306 are stationary. Wheel mount 304 includes a plurality of gear wheels 316 mounted about the periphery of the wheel mount 304. Gear wheels 316 rotate about their respective individual axes. Any means for mounting gear wheels 316 to wheel mount 304 are envisioned. Each gear wheel 316 includes slotted opening 318 extending transverse to the axis of rotation of the gear wheels 316. Slotted openings 318 receive the ends of tensioning members 182 of liner base 104. The extreme ends of tensioning members 182 are secured to wheel mount 304 by secured engagement with suture mounts 320 disposed about the periphery of wheel mount 304.

Gear ring 308 includes a plurality of gear teeth 322 depending from its lower surface (FIG. 29). Gear teeth 322 engage the teeth of gear wheels 316 during rotation of gear ring 308 relative to wheel mount 304 and wheel hub 308. Gear ring 308 also includes tab 324. Tab 324 may be spring biased radially inwardly and is adapted to be received within corresponding openings 326 of gear hub 306 upon rotation of the gear ring 308. In this manner, gear ring 308 may be selectively secured at desired rotational orientations relative to gear wheel 304 and gear hub 306.

Liner base 104 of access apparatus 300 is identical to the liner base 104 described in connection with FIG. 1.

Figure 32:
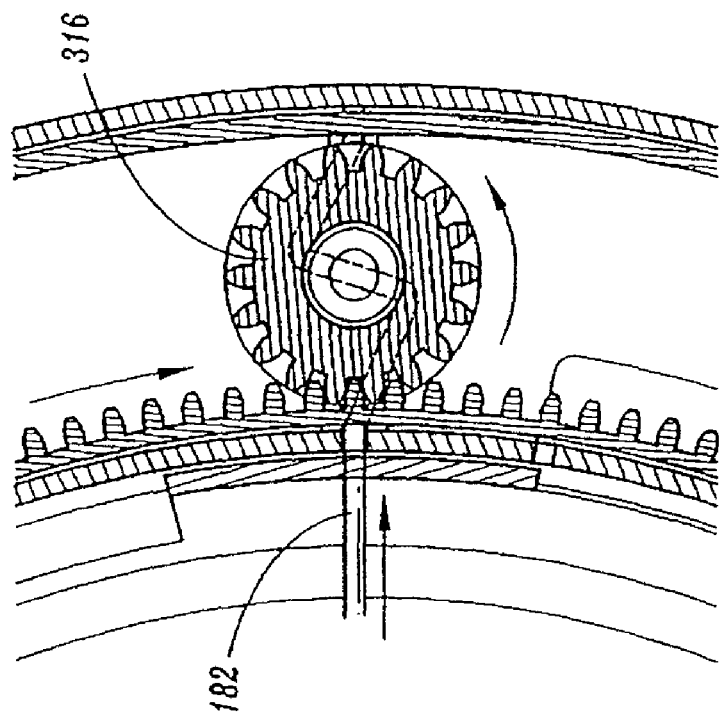
FIGS. 31-32 are side cross-sectional view illustrating operation of the gear wheels during rotation of the gear ring of the access housing of FIG. 27.
Figure 31:
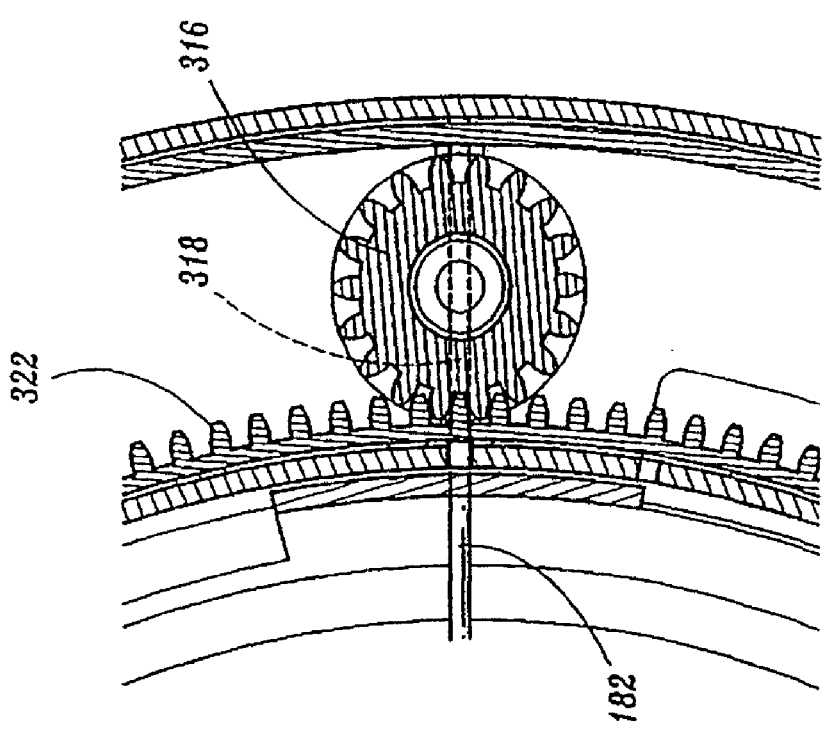

FIGS. 31-32 illustrate operation of access apparatus 300. Subsequent to positioning liner base 104 within the incision, gear ring 308 is rotated in the direction of the directional arrow shown in FIG. 32 to cause gear wheels 316 to rotate about their respective axes. This rotation causes displacement of tensioning members 182 in the manner depicted in FIG. 32 to thereby impart a tensioning affect on the tensioning members 182. Desirably, the gear wheels 316 include an integral spool for winding the tensioning members. Inner ring 170 of liner base 104 is thus drawn upwardly preferably in engagement with the body cavity wall. In addition, such action causes sleeve 168 of liner base 104 to retract tissue in the manner previously described in connection with FIG. 1. As noted, tab 324 of gear ring 308 selectively secures the gear ring 308 at a desired rotational relationship relative to gear wheel 304 and gear hub 306. If greater tension or retraction is required, gear ring may be further rotated to permit tab 324 to be received in the next successive opening 326 of gear hub 306.

Thus, the access apparatus of the present disclosure provides for selective retraction of tissue during a hand-assisted laparoscopic surgical technique. Moreover, the apparatus may be utilized in conjunction with hand-assisted laparoscopic procedures and more conventional instrument-assisted laparoscopic procedures. This flexibility and adaptability significantly reduces the number of incisions required within the abdominal cavity thus minimizing patient trauma and infection, and improving recovery time.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical access system, which comprises:
    an access member including:
        lower and upper segments;
        a sleeve segment including a flexible membrane extending between the lower and upper segments, the sleeve segment dimensioned and adapted for positioning through a tissue tract to substantially line the tissue tract;
        an access housing mounted to the sleeve segment, the sleeve segment and the access housing defining a passage therethrough; and
        an access seal mounted to the access housing, the access seal dimensioned and adapted to establish a substantial seal about an arm or hand of a clinician; and
    a trocar adapter releasably connectable to the access housing in the absence of the arm or hand of the clinician, and having;
        a trocar sleeve dimensioned for reception of a surgical instrument, the trocar sleeve at least partially disposed within the passage of the access member when the trocar adapter is mounted to the access housing;
        a trocar housing having a trocar seal dimensioned and adapted to establish a substantial seal about the surgical instrument, the trocar sleeve extending from the trocar housing, the trocar adapter including an adapter base, the adapter base adapted to releasably mount to the access housing of the access member.

2. The surgical access system according to claim 1 wherein at least one of the trocar housing and trocar sleeve are connected to an internal area of the adapter base.

* * * * *